(12) United States Patent
Teich et al.

(10) Patent No.: US 9,784,763 B1
(45) Date of Patent: Oct. 10, 2017

(54) SHIELDED PROBE SYSTEMS WITH CONTROLLED TESTING ENVIRONMENTS

(71) Applicant: Cascade Microtech, Inc., Beaverton, OR (US)

(72) Inventors: Michael Teich, Moritzburg (DE); Karsten Stoll, Sohland an der Spree (DE); Walter Matthias Clauss, Radeberg (DE); Swen Schmiedchen, Dresden (DE)

(73) Assignee: Cascade Microtech, Inc., Beaverton, OR (US)

( * ) Notice: Subject to any disclaimer, the term of this patent is extended or adjusted under 35 U.S.C. 154(b) by 39 days.

(21) Appl. No.: 15/094,716

(22) Filed: Apr. 8, 2016

(51) Int. Cl.
| | |
|---|---|
| *G01R 31/10* | (2006.01) |
| *G01R 1/18* | (2006.01) |
| *G01R 1/067* | (2006.01) |
| *G01R 1/44* | (2006.01) |
| *G01R 1/073* | (2006.01) |
| *G01N 27/42* | (2006.01) |
| *G01N 31/02* | (2006.01) |

(52) U.S. Cl.
CPC ............ *G01R 1/18* (2013.01); *G01R 1/06711* (2013.01); *G01R 1/07392* (2013.01); *G01R 1/44* (2013.01); *G01N 27/42* (2013.01); *G01N 31/02* (2013.01)

(58) Field of Classification Search
CPC ............ G01R 1/07392; G01R 31/2889; G01R 31/002; G01R 31/00; G01N 27/42; G01N 31/02

USPC ......... 324/71, 378, 403, 415, 425, 500, 537, 324/750.14
See application file for complete search history.

(56) References Cited

U.S. PATENT DOCUMENTS

| | | |
|---|---|---|
| 4,115,736 A | 9/1978 | Tracy |
| 5,266,889 A | 11/1993 | Harwood et al. |
| 5,345,170 A | 9/1994 | Schwindt et al. |
| 7,579,854 B2 | 8/2009 | Kiesewetter et al. |
| 8,497,693 B2 | 7/2013 | Kiesewetter et al. |
| 2001/0001538 A1* | 5/2001 | Harwood ........... G01R 1/06705 324/750.14 |
| 2005/0287685 A1* | 12/2005 | McFadden ......... G01R 31/2874 438/17 |
| 2007/0205784 A1 | 9/2007 | Dunklee |
| 2007/0247178 A1 | 10/2007 | Dunklee et al. |
| 2008/0042680 A1 | 2/2008 | Cowan et al. |

(Continued)

*Primary Examiner* — Jermele M Hollington
*Assistant Examiner* — Raul Rios Russo
(74) *Attorney, Agent, or Firm* — Dascenzo Intellectual Property Law, P.C.

(57) ABSTRACT

Shielded probe systems are disclosed herein. The shielded probe systems are configured to test a device under test (DUT) and include an enclosure that defines an enclosure volume, a translation stage with a stage surface, a substrate-supporting stack extending from the stage surface, an electrically conductive shielding structure, an isolation structure, and a thermal shielding structure. The substrate-supporting stack includes an electrically conductive support surface and a temperature-controlled chuck. The electrically conductive shielding structure defines a shielded volume. The isolation structure electrically isolates the electrically conductive shielding structure from the enclosure and from the translation stage. The thermal shielding structure extends within the enclosure volume and at least partially between the enclosure and the substrate-supporting stack.

20 Claims, 3 Drawing Sheets

(56) References Cited

U.S. PATENT DOCUMENTS

2008/0048693 A1 2/2008 Peters et al.
2013/0075982 A1* 3/2013 Simmons ........... G01R 31/2865
    279/3

* cited by examiner

SHIELDED PROBE SYSTEMS WITH CONTROLLED TESTING ENVIRONMENTS

FIELD OF THE DISCLOSURE

The present disclosure relates generally to shielded probe systems and more specifically to shielded probe systems that utilize a shielding structure to shield a testing environment from an ambient environment that surrounds the probe system.

BACKGROUND OF THE DISCLOSURE

Probe systems may be utilized to test operation and/or performance of a device under test (DUT). Probe systems generally include one or more probes that may be configured to provide a test signal to the DUT and/or to receive a resultant signal from the DUT. By measuring the response of the DUT to the test signal (e.g., by measuring and/or quantifying the resultant signal), the operation and/or performance of the DUT may be quantified.

Under certain circumstances, it may be desirable to test the DUT under controlled environmental conditions. As examples, it may be desirable to test the DUT under controlled thermal conditions, under controlled light conditions, and/or under controlled atmospheric conditions, such as to quantify operation and/or performance of the DUT under these controlled environmental conditions. Additionally or alternatively, it also may be desirable to test the DUT under low noise conditions, such as by limiting electromagnetic interference (EMI) with the testing process and/or by limiting electromagnetic radiation and/or electric fields within the testing environment. Thus, there exists a need for improved shielded probe systems.

SUMMARY OF THE DISCLOSURE

Shielded probe systems are disclosed herein. The shielded probe systems, which also may be referred to herein as a probe system, are configured to test a device under test (DUT) and include an enclosure that defines an enclosure volume. The probe systems also include a translation stage including a stage surface that extends within the enclosure volume and a substrate-supporting stack extending from the stage surface. The substrate-supporting stack includes an electrically conductive support surface, which is configured to support a substrate that includes the DUT, and a temperature-controlled chuck, which is configured to regulate a temperature of the electrically conductive support surface.

The probe systems further include an electrically conductive shielding structure extending within the enclosure volume. The electrically conductive shielding structure defines a shielded volume that is a subset of the enclosure volume and that contains the electrically conductive support surface. The electrically conductive shielding structure extends between the electrically conductive support surface and the enclosure, the translation stage, and the temperature-controlled chuck.

The probe systems further include an isolation structure and a thermal shielding structure. The isolation structure electrically isolates the electrically conductive shielding structure from the enclosure and from the translation stage. The thermal shielding structure extends within the enclosure volume and at least partially between the enclosure and the substrate-supporting stack.

DETAILED DESCRIPTION AND BEST MODE OF THE DISCLOSURE

Figure 1:
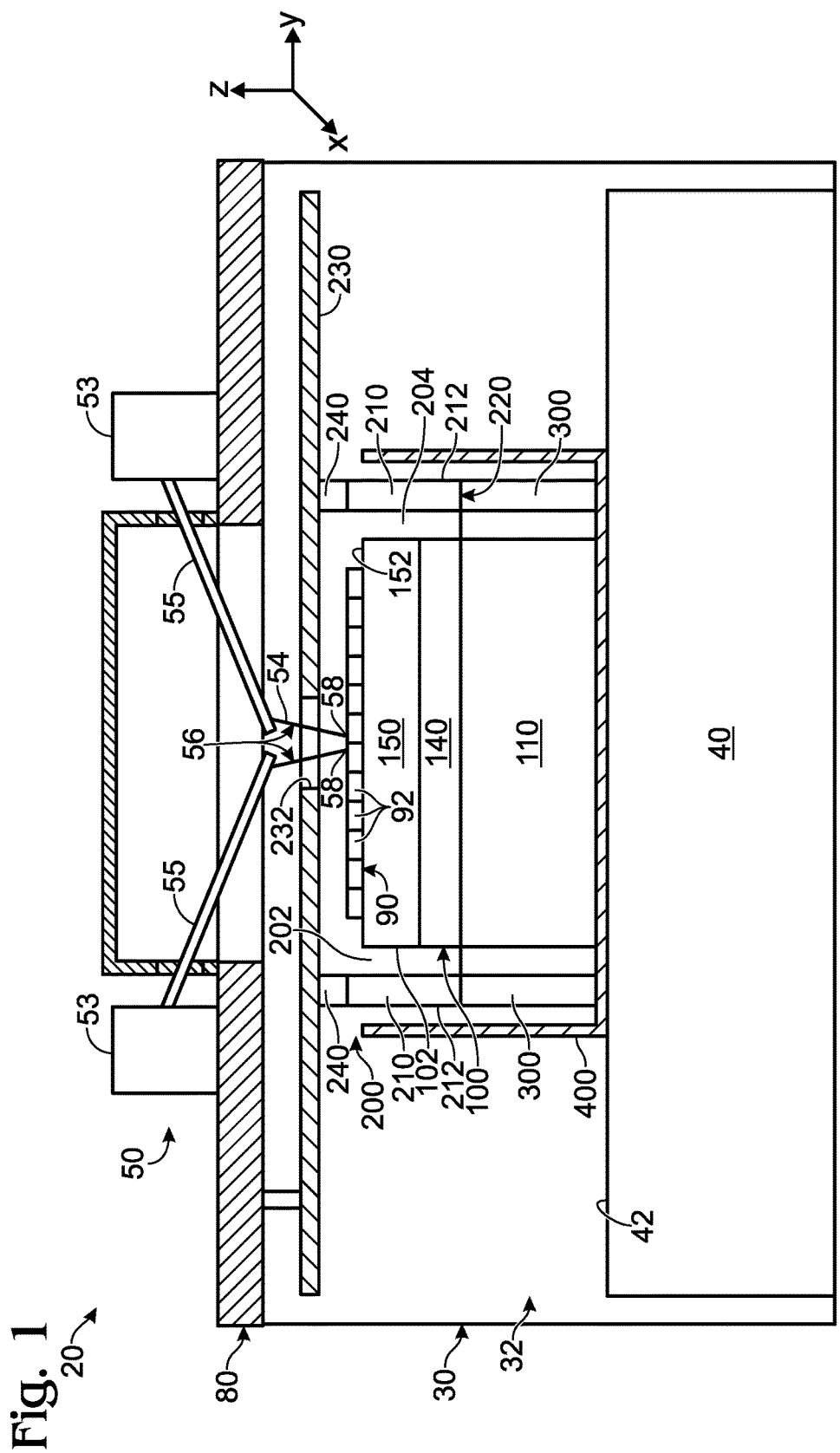
FIG. 1 is a less schematic cross-sectional view of a portion of a shielded probe system according to the present disclosure.
Figure 2:
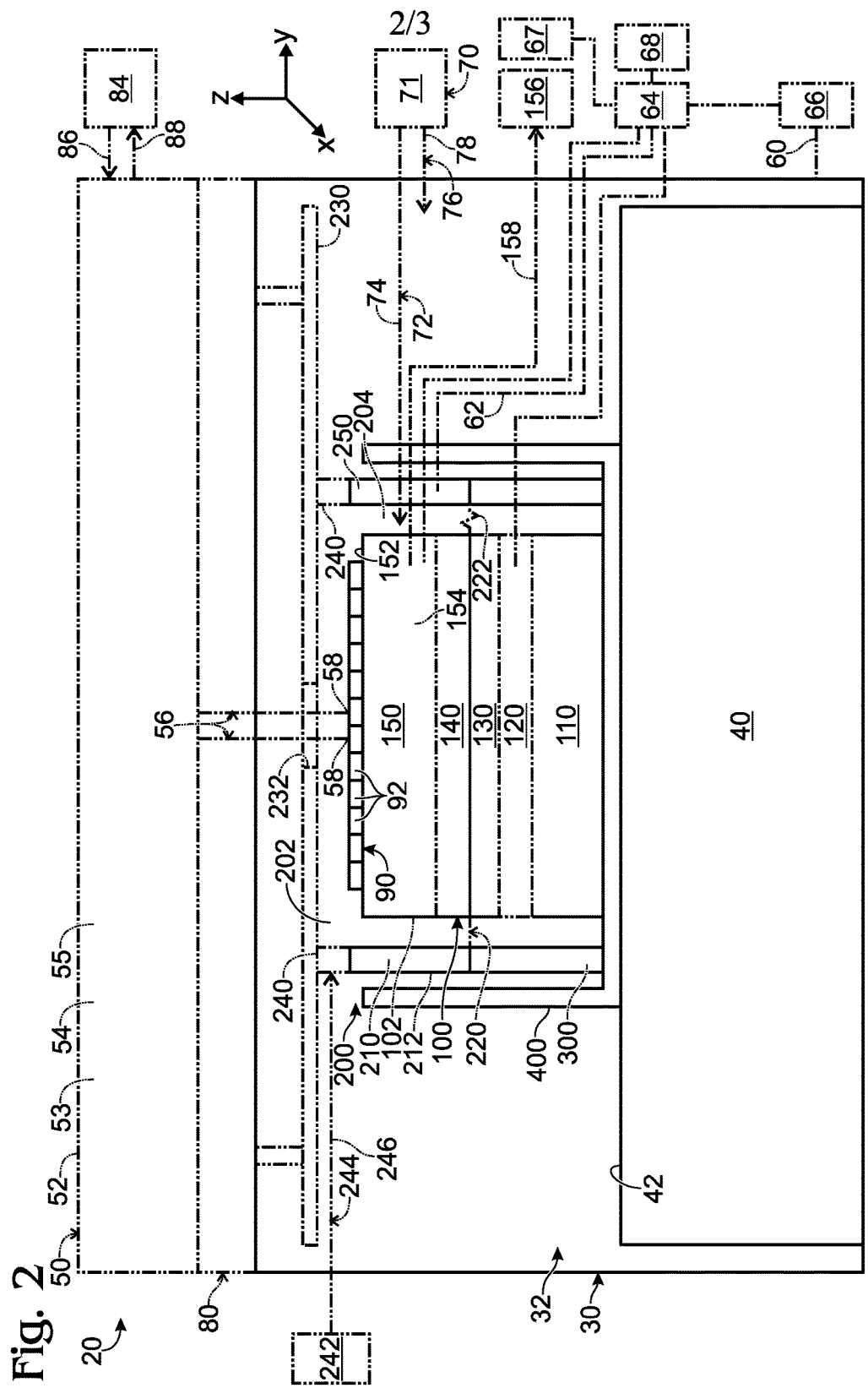
FIG. 2 is a schematic representation of shielded probe systems according to the present disclosure.
Figure 3:
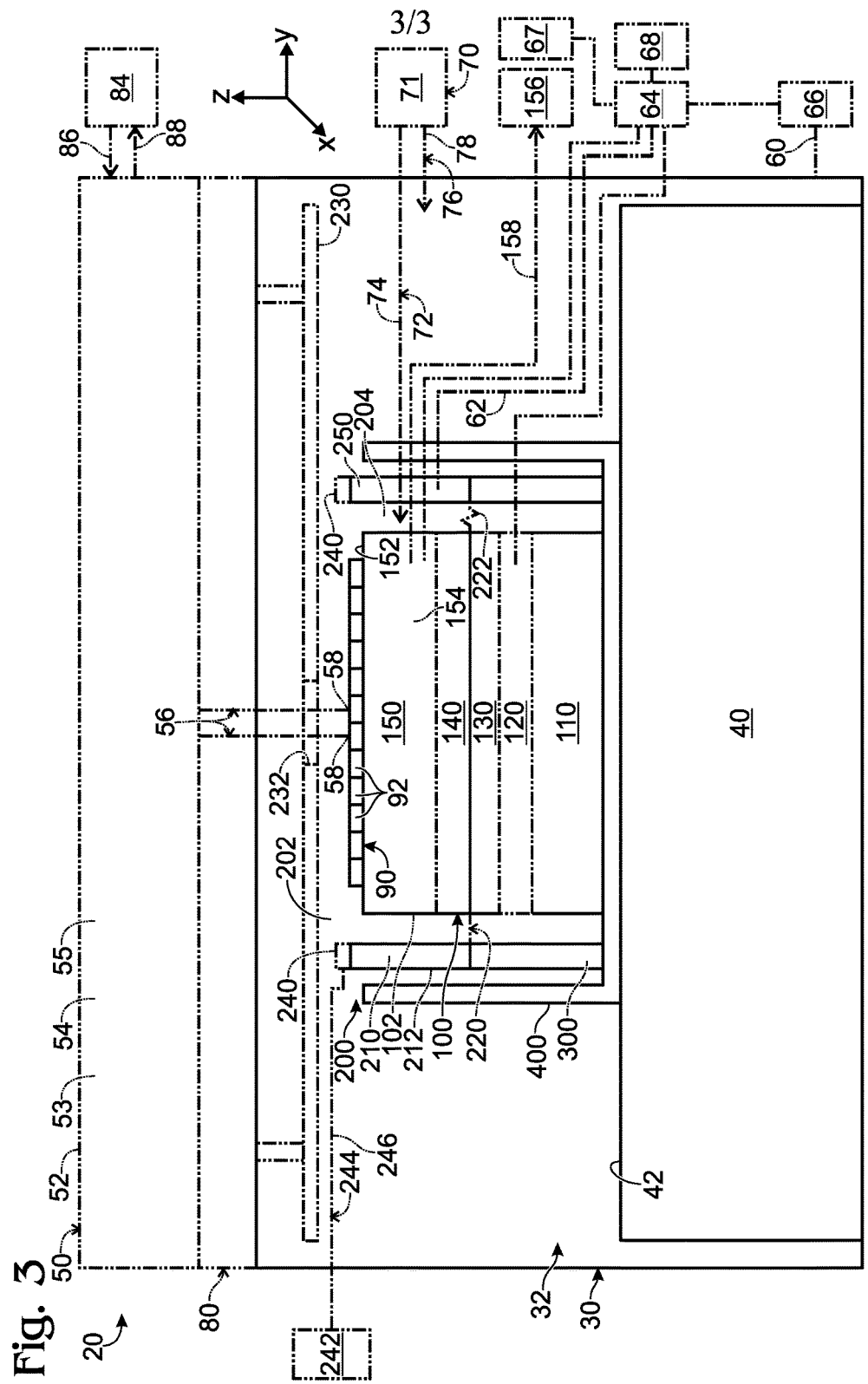
FIG. 3 is a schematic representation of shielded probe systems according to the present disclosure.

FIGS. 1-3 provide examples of shielded probe systems 20 according to the present disclosure. Elements that serve a similar, or at least substantially similar, purpose are labeled with like numbers in each of FIGS. 1-3, and these elements may not be discussed in detail herein with reference to each of FIGS. 1-3. Similarly, all elements may not be labeled in each of FIGS. 1-3, but reference numerals associated therewith may be utilized herein for consistency. Elements, components, and/or features that are discussed herein with reference to one or more of FIGS. 1-3 may be included in and/or utilized with any of FIGS. 1-3 without departing from the scope of the present disclosure. In general, elements that are likely to be included in a particular embodiment are illustrated in solid lines, while elements that are optional are illustrated in dash-dot-dot lines. However, elements that are shown in solid lines may not be essential and, in some embodiments, may be omitted without departing from the scope of the present disclosure.

FIG. 1 is a representation of a shielded probe system 20 according to the present disclosure, while FIGS. 2-3 provide more schematic representations of additional embodiments of shielded probe systems 20 according to the present disclosure. Shielded probe systems 20 also may be referred to herein as a shielded probe system 20, a test system 20, a probe system 20, and/or a system 20. Probe systems 20 may be adapted, configured, designed, shaped, sized, and/or constructed to test one or more devices under test (DUTs) 92, which may be formed on, supported by, and/or included in a substrate 90.

As illustrated in FIGS. 1-3, probe systems 20 include an enclosure 30 that at least partially bounds, or defines, an enclosure volume 32. Enclosure volume 32 may be adapted, configured, designed, shaped, sized, and/or constructed to receive substrate 90 and/or DUT 92.

Probe systems 20 further may include a contacting assembly 50 configured to contact DUT 92 with one or more probes 56. As illustrated in FIGS. 1-3, contacting assembly 50 may include one or more probe arms 55, one or more probes 56 with a corresponding one or more probe tips 58, and/or one or more manipulators 53. Manipulator 53 may be external to enclosure volume 32, such that probe 56 may be oriented within enclosure volume 32 and probe arm 55 may operatively connect manipulator 53 to probe 56. Probe 56 may include, and/or be, a needle probe 54. In addition, and as illustrated, at least a portion of contacting assembly 50 may extend through and/or within an aperture 232.

As illustrated in FIGS. 1-3, probe systems 20 further include an electrically conductive shielding structure 200, which may be configured to provide electromagnetic shielding to a shielded volume 202. Additionally, probe systems 20 include a thermal shielding structure 400, which may be configured to provide thermal shielding to shielded volume 202.

As also illustrated in FIGS. 1-3, probe systems 20 further include a substrate-supporting stack 100 that includes an electrically conductive support surface 152 configured to support substrate 90 and/or DUT 92. Substrate-supporting stack 100 also may be referred to herein as a chuck assembly 100, a substrate-supporting chuck assembly 100, and/or a substrate-supporting assembly 100. Electrically conductive support surface 152 also may be referred to herein as a support surface 152.

As also illustrated in FIGS. 1-3, probe systems 20 include a translation stage 40 extending within enclosure volume 32. Translation stage 40 includes a stage surface 42 configured to support substrate-supporting stack 100. Translation stage 40 may be configured to operatively translate substrate-supporting stack 100 relative to probes 56 and/or to operatively rotate substrate-supporting stack 100 relative to probes 56, such as to facilitate alignment between one or more DUTs 92 and probes 56. Translation stage 40 is at least partially, or even fully, external to shielded volume 202.

Substrate-supporting stack 100 extends from stage surface 42 and at least partially within shielded volume 202 of enclosure volume 32. Substrate-supporting stack 100 includes a temperature-controlled chuck 110 configured to regulate a temperature of support surface 152, and thereby to regulate a temperature of substrate 90 and/or DUTs 92. Temperature-controlled chuck 110 also may be referred to herein as a thermal chuck 110 and/or as a chuck 110. Temperature-controlled chuck 110 is at least partially, or even fully, external to shielded volume 202.

Probe systems 20 further include an isolation structure 300 that electrically isolates electrically conductive shielding structure 200 from enclosure 30 and from translation stage 40. As illustrated, isolation structure 300 may be at least partially, or even fully, external to shielded volume 202. Isolation structure 300 may extend between at least a portion of shielding structure 200 and translation stage 40, and/or may spatially separate shielding structure 200 from translation stage 40. Isolation structure 300 may be operatively attached to stage surface 42 of translation stage 40, and/or may be operatively attached to shielding structure 200. Isolation structure 300 may be formed from any appropriate material, and may include, or be, an electrically insulating material and/or a thermally insulating material.

Probe systems 20 further include thermal shielding structure 400 extending within enclosure volume 32 and at least partially between enclosure 30 and substrate-supporting stack 100. Thermal shielding structure 400 may surround at least a portion of shielding structure 200, such as to at least partially thermally isolate shielded volume 202 from a remainder of enclosure volume 32. Thermal shielding structure 400 may be formed from any appropriate material, and may include, or be, a thermally insulating material.

Probe systems 20 according to the present disclosure may be configured to provide environmental shielding to shielded volume 202 via a plurality of distinct structures. As examples, electrically conductive shielding structure 200 may be configured to provide electromagnetic shielding to shielded volume 202, and thermal shielding structure 400 may be configured to provide thermal shielding to shielded volume 202. Additionally, isolation structure 300 may be configured to electrically isolate shielding structure 200, such as to facilitate applying an electrical bias to shielding structure 200. Because probe systems 20 according to the present disclosure utilize distinct electromagnetic shielding elements and thermal shielding elements, each of shielding structure 200, isolation structure 300, and thermal shielding structure 400 may be individually configured to exhibit a specific respective shielding characteristic.

Additionally, probe systems 20 according to the present disclosure may be configured such that shielded volume 202 has a size, shape, and/or orientation that facilitates electromagnetic, thermal, and/or environmental shielding thereof. Additionally or alternatively, utilizing a plurality of distinct shielding elements may allow for control of a testing environment within shielded volume 202 to a higher degree of precision and/or accuracy relative to traditional probe systems.

During operation of probe system 20 of FIG. 1, manipulator 53 may be utilized to operatively translate needle probes 54 throughout a needle probe range-of-motion, thereby operatively translating probe tips 58 relative to DUT 92. As an example, one or more manipulators 53 may be utilized to operatively align one or more probe tips 58 with specific, target, and/or desired locations on DUT 92, such as to permit communication between the corresponding probes and the DUT. This may include operative translation of probes 56 in a plurality of different, separate, distinct, perpendicular, and/or orthogonal directions, such as the X, Y, and/or Z-directions that are illustrated in FIGS. 1-3. In the example of FIGS. 1-3, the X and Y-directions may be parallel, or at least substantially parallel, to an upper surface of substrate 90, while the Z-direction may be perpendicular, or at least substantially perpendicular, to the upper surface of substrate 90. However, this specific configuration is not required.

As discussed, probe systems 20 include electrically conductive shielding structure 200. Electrically conductive shielding structure 200 also may be referred to herein as a shielding structure 200. Shielding structure 200 may extend between enclosure 30, or at least a portion of enclosure 30, and support surface 152, or at least a portion of support surface 152.

Shielding structure 200 may be adapted, configured, designed, shaped, sized, and/or constructed to shield shielded volume 202, which is a subset of enclosure volume 32. This may include shielding the shielded volume from an ambient environment, and the ambient environment may surround enclosure 30 and/or shielding structure 200, may be external to enclosure 30 and/or shielding structure 200, and/or may be external to enclosure volume 32 and/or shielded volume 202. As examples, shielding structure 200 may shield the shielded volume from electromagnetic radiation that may be present in the ambient environment, from electric fields that may be present within the ambient environment, from magnetic fields that may be present in the ambient environment, and/or from visible light that may be present within the ambient environment.

Shielded volume 202 may include and/or be any appropriate fraction of enclosure volume 32. As examples, a ratio of a volume of shielded volume 202 to a volume of enclosure volume 32 may be at least 0.001, at least 0.005, at least 0.01, at least 0.05, at least 0.1, at least 0.15, at least 0.2, at least 0.25, at most 0.5, at most 0.4, at most 0.3, at most 0.25, at most 0.2, at most 0.15, and/or at most 0.1.

The specific ratio between the volume, or magnitude, of shielded volume 202 and the volume, or magnitude, of enclosure volume 32 may be selected and/or specified based upon one or more design criteria. As examples, the ratio may be selected and/or specified based upon a distance that translation stage 40 moves in the X-direction and in the Y-directions and/or based upon a diameter of substrate 90. As another example, the distance that translation stage 40 moves in the X-direction and in the Y-direction may dictate a minimum value for the volume of enclosure volume 32, or at least a minimum value for a cross-sectional area of enclosure volume 32 as measured in the X-Y plane. This distance generally is at least twice the diameter of substrate 90. As yet another example, and since substrate 90 extends within shielded volume 202, the minimum value for the cross-sectional area of shielded volume 202, as measured in the X-Y plane, may be greater than the area of an upper surface of substrate 90.

Substrate-supporting stack 100 additionally may include an electrically conductive upper stack layer 150, which defines electrically conductive support surface 152, and an upper electrically insulating layer 140, which extends between temperature-controlled chuck 110 and electrically conductive upper stack layer 150. Electrically conductive upper stack layer 150 also may be referred to herein as an upper stack layer 150, an upper chuck assembly layer 150, and/or an upper substrate-supporting layer 150. Upper stack layer 150 may be metallic and/or may be thermally conductive.

As illustrated in FIGS. 1-3, upper electrically insulating layer 140 additionally may extend between upper stack layer 150 and at least a portion of shielding structure 200. More specifically, upper electrically insulating layer 140 may be a thermally conductive layer configured to facilitate thermal exchange between temperature-controlled chuck 110 and upper stack layer 150 but to resist electrical communication therebetween.

Shielding structure 200 extends between electrically conductive support surface 152 and enclosure 30, between the electrically conductive support surface and translation stage 40, and between the electrically conductive support surface and temperature-controlled chuck 110. Shielding structure 200 may shield shielded volume 202 and/or support surface 152 that extends therein in any suitable manner. As examples, shielding structure 200 may be metallic and/or metal-coated, may be electrically grounded, and/or may be electrically biased to a target potential.

Additionally, shielding structure 200 may be adapted, configured, designed, shaped, sized, and/or constructed to restrict, limit, block, and/or occlude fluid flow between shielded volume 202 and a remainder of enclosure volume 32. Such a configuration may permit one or more environmental conditions within shielded volume 202 to be maintained differently from corresponding environmental conditions within a remainder of enclosure volume 32 and/or within an ambient environment that surrounds probe system 20 and/or that is external to enclosure volume 32. Examples of the one or more environmental conditions include one or more of a humidity within the shielded volume, a temperature within the shielded volume, and/or a gas composition within the shielded volume.

Shielding structure 200 may restrict the fluid flow in any suitable manner. As an example, shielding structure 200 may be configured to restrict, limit, block, and/or occlude fluid flow into shielded volume 202. As another example, shielding structure 200 may be configured to restrict, limit, block, and/or occlude diffusion of moisture into shielded volume 202.

Shielding structure 200, or shielding structure 200 in combination with enclosure 30, additionally or alternatively may be adapted, configured, designed, sized, and/or constructed to restrict, limit, block, and/or occlude transmission of ambient light into shielded volume 202. As examples, shielding structure 200, or the combination of shielding structure 200 and enclosure 30, may be configured to attenuate the ambient light that passes from an ambient environment into shielded volume 202 by at least 100 decibels (dB), by at least 110 dB, by at least 120 dB, by at least 130 dB, and/or by at least 140 dB. This attenuation of ambient light also may be referred to herein as shielding the shielded volume from ambient, or visible, light that may be present within the ambient environment.

Stated another way, shielding structure 200 may include and/or may be formed from a light-absorbing material that absorbs light that may be incident thereon and that thereby restricts, limits, blocks, and/or occludes transmission of ambient light into shielded volume 202. Additionally or alternatively, shielding structure 200 may include and/or be formed from a light-reflecting material that reflects light that may be incident thereon and that thereby restricts, limits, blocks, and/or occludes transmission of ambient light into shielded volume 202.

As illustrated in FIGS. 1-3, shielding structure 200 may include an electrically conductive peripheral shield 210 that may be spaced-apart from substrate-supporting stack 100. Electrically conductive peripheral shield 210 also may be referred to herein as a peripheral shield 210. Peripheral shield 210 may have an external shield periphery 212 and may extend around an external stack periphery 102 of substrate-supporting stack 100. Peripheral shield 210 and substrate-supporting stack 100 thus may together define an annular region 204 that defines at least a portion of shielded volume 202.

Shielding structure 200 additionally may include a flexible, electrically conductive lower shield 220 that extends between substrate-supporting stack 100 and peripheral shield 210. Electrically conductive lower shield 220 also may be referred to herein as a lower shield 220. Lower shield 220 may be configured to fluidly isolate shielded volume 202 from temperature-controlled chuck 110, such as to minimize and/or prevent fluid flow between shielded volume 202 and temperature-controlled chuck 110. Additionally or alternatively, lower shield 220 may extend between, or at least partially between, temperature controlled chuck 110 and support surface 152. Additionally or alternatively, lower shield 220 may be configured to limit heat transfer between substrate-supporting stack 100 and/or temperature-controlled chuck 110 thereof and peripheral shield 210. Lower shield 220 may be constructed of any appropriate material and may include a metal foil, a metallic foil, a nickel foil, a metal-coated membrane, and/or an electrically conductive membrane.

Probe system 20 additionally may include an electrically conductive upper shield 230 that extends above, or is opposed to, support surface 152. Electrically conductive upper shield 230 also may be referred to herein as an upper shield 230. Upper shield 230 may include aperture 232, which may be sized to permit at least one probe 56, a plurality of probes 56, and/or a plurality of spaced-apart probes 56, to extend therethrough.

Shielding structure 200 additionally may include an electrically conductive gasket 240 that extends between peripheral shield 210 and upper shield 230. Electrically conductive gasket 240 also may be referred to herein as a shielding gasket 240 and/or as a gasket 240. Electrically conductive gasket 240 may be configured to form an at least partial fluid seal between peripheral shield 210 and upper shield 230, such as to minimize and/or prevent fluid flow between shielded volume 202 and a remainder of enclosure volume 32. Additionally or alternatively, electrically conductive gasket 240 may be configured to restrict electromagnetic radiation from entering shielded volume 202, such as from enclosure volume 32.

Electrically conductive gasket 240 is configured to selectively contact upper shield 230 to form the at least partial fluid seal and/or an electromagnetic shield between peripheral shield 210 and upper shield 230, and may include any appropriate material of construction. For example, electrically conductive gasket 240 may include, or be, a resilient gasket, such as a foam gasket. Additionally or alternatively, electrically conductive gasket 240 may include, or be, an inflatable gasket configured to be selectively inflated to selectively contact upper shield 230 and selectively deflated to retract from upper shield 230.

As illustrated in FIGS. 1-3, probe system 20 additionally may include a platen 80 that extends above electrically conductive support surface 152 and that is configured to support contacting assembly 50, or at least a portion of contacting assembly 50. For example, and as illustrated in FIG. 1, manipulator 53 may be operatively attached to platen 80.

FIGS. 2-3 further illustrate additional and/or optional structures, components, and/or features that may be included in and/or utilized with probe systems 20 according to the present disclosure. Any of the structures, components, and/or features that are discussed herein with reference to FIGS. 2-3 may be included in and/or utilized with probe system 20 of FIG. 1 without departing from the scope of the present disclosure. Similarly, any of the structures, components, and/or features that are discussed herein with reference to FIG. 1 may be included in and/or utilized with probe systems 20 of FIGS. 2-3 without departing from the scope of the present disclosure.

Lower shield 220 may be sufficiently flexible to permit relative motion between peripheral shield 210 and substrate-supporting stack 100 such that lower shield 220 may provide uninterrupted electromagnetic and/or thermal shielding as a relative position of substrate-supporting stack 100 and shielding structure 200 is varied, such as due to a thermal expansion and/or contraction of substrate-supporting stack 100, of shielding structure 200, and/or of isolation structure 300. Thus, lower shield 220 may include at least one expansion region 222 configured to permit relative motion between peripheral shield 210 and substrate-supporting stack 100. For example, expansion region 222 may be configured to expand and/or to contract to permit relative motion between peripheral shield 210 and substrate-supporting stack 100, and may include at least one pleat.

As discussed, and as illustrated in FIGS. 1-3, electrically conductive gasket 240 may be configured to selectively contact upper shield 230 and retract from upper shield 230. Stated differently, shielding structure 200 may be configured to selectively contact electrically conductive gasket 240 with upper shield 230 and/or to selectively retract electrically conductive gasket 240 from upper shield 230, such as to permit relative motion between substrate-supporting stack 100 and contacting assembly 50. Specifically, FIGS. 1-2 illustrate electrically conductive gasket 240 in contact with upper shield 230, while FIG. 3 illustrates electrically conductive gasket 240 retracted from the electrically conductive upper shield.

Electrically conductive gasket 240 may be brought into contact with upper shield 230 and/or removed from contact with upper shield 230 in any appropriate manner. For example, and as illustrated in FIG. 2, electrically conductive gasket 240 may include, or be, an inflatable gasket, and probe system 20 additionally may include a pressurizing fluid source 242 configured to selectively inflate the inflatable gasket and to selectively deflate the inflatable gasket. Pressurizing fluid source 242 may be configured to produce, supply, deliver, and/or control a flow of a pressurizing fluid stream 246 through a pressurizing fluid conduit 244 operatively coupled to pressurizing fluid source 242 and electrically conductive gasket 240.

Additionally or alternatively, shielding structure 200 may include a drive mechanism 250 configured to selectively contact electrically conductive gasket 240 with upper shield 230 and/or to selectively retract electrically conductive gasket 240 from upper shield 230. Drive mechanism 250 may include, or be, any appropriate mechanism, and may be coupled to, integrated into, and/or at least partially enclosed by peripheral shield 210.

Additionally or alternatively, translation stage 40 may be configured to selectively contact electrically conductive gasket 240 with upper shield 230 and/or to selectively retract electrically conductive gasket 240 from upper shield 230. For example, translation stage 40 may be configured to translate shielding structure 200 in at least the Z-direction as illustrated in FIGS. 1-3 to selectively establish and/or cease mechanical and/or electrical contact between electrically conductive gasket 240 and upper shield 230.

As discussed, and with continued reference to FIGS. 2-3, thermal shielding structure 400 may be spaced-apart from external shield periphery 212 of peripheral shield 210. However, this is not required, and it is within the scope of the present disclosure that shielding structure 400 additionally or alternatively may be in direct physical contact with external shield periphery 212 of peripheral shield 210. As illustrated in FIGS. 1-3, thermal shielding structure 400 may extend between at least a portion of shielding structure 200 and at least a portion of enclosure 30. Additionally or alternatively, thermal shielding structure 400 may extend between temperature-controlled chuck 110 and/or translation stage 40. Thermal shielding structure 400 may be operatively attached to stage surface 42 of translation stage 40, and/or may be operatively attached to substrate-supporting stack 100. Additionally or alternatively, isolation structure 300 may be integrally formed with, form a portion of, and/or be operatively coupled to thermal shielding structure 400.

Enclosure 30 may be an electrically conductive enclosure, and/or may be configured to at least partially shield enclosure volume 32 from the ambient environment that surrounds enclosure 30, that is external to enclosure 30, and/or that is external to enclosure volume 32. As examples, enclosure 30 may shield enclosure volume 32 from electromagnetic radiation that may be present within the ambient environment, from electric fields that may be present within the ambient environment, from magnetic fields that may be present within the ambient environment, and/or from visible light that may be present within the ambient environment.

As a more specific example, and with reference to FIGS. 2-3, probe system 20 additionally may include a shield conductor 60 in electrical communication with enclosure 30. As used herein, the term "electrical communication" may be used to describe an electrical coupling and/or an electrical connection through which an electric current may pass. Additionally or alternatively, the term "electrical communication" may be used herein to describe an electrical connection that may be characterized by a net electrical resistance of less than 10 Ohms, less than 5 Ohms, less than 1 Ohm, less than 0.5 Ohm, and/or less than 0.1 Ohm. Additionally or alternatively, as used herein, the term "direct electrical communication" may be used to describe an electrical coupling and/or an electrical connection that is physically, mechanically, and/or operatively connected to each element said to be in direct electrical communication.

In an embodiment in which enclosure 30 is an electrically conductive enclosure, shield conductor 60 may be configured to maintain enclosure 30 at a predetermined and/or user-configurable shield potential and/or to electrically ground enclosure 30. For example, probe system 20 additionally may include a shield potential generator 66 configured to generate the shield potential, and shield conductor 60 may be in electrical communication with shield potential generator 66 and enclosure 30.

Similarly, and as illustrated in FIGS. 2-3, probe system 20 may include a guard conductor 62 in electrical communication with shielding structure 200 and configured to maintain shielding structure 200 at a predetermined and/or user-configurable guard potential and/or to electrically ground shielding structure 200. For example, probe system 20 additionally may include a guard potential generator 68 configured to generate the guard potential, and guard conductor 62 may be in electrical communication with guard potential generator 68 and shielding structure 200.

The guard potential may be equal, or at least substantially equal, to the shield potential, or the guard potential may be different than the shield potential. In an embodiment in which the guard potential is equal, or at least substantially equal, to the shield potential, shield potential generator 66 and guard potential generator 68 may refer to a single potential generator. Probe system 20 additionally may include a switching structure 64 configured to selectively apply the guard potential to guard conductor 62 and to selectively ground guard conductor 62. Switching structure 64 may be configured to selectively apply the shield potential to shield conductor 60 and/or to selectively ground shield conductor 60. Switching structure 64 additionally or alternatively may be configured to electrically interconnect electrically conductive upper chuck layer 120 and/or electrically conductive upper stack layer 150 with a signal generator/measuring unit 67. Signal generator/measuring unit 67 may be configured to provide any suitable signal to upper chuck layer 120, to provide any suitable signal to electrically conductive upper stack layer 150, to receive any suitable signal from upper chuck layer 120, and/or to receive any suitable signal from electrically conductive upper stack layer 150. Switching structure 64 may include, or be, any appropriate mechanism, such as an electrical switch, an electrical relay, and/or a solid-state relay.

In addition to shielding shielded volume 202 from electrical and/or thermal disturbances, probe system 20 additionally may be configured to provide, modify, control, and/or regulate an atmospheric environment within shielded volume 202. For example, and with reference to FIGS. 2-3, probe system 20 additionally may include an environmental control assembly 70 that is configured to regulate a chemical composition of a testing environment that extends within shielded volume 202. The testing environment may occupy a portion of, a majority of, and/or an entirety of shielded volume 202. Specifically, environmental control assembly 70 may be configured to provide a purge gas stream 74 to shielded volume 202 to regulate the chemical composition of the testing environment, for example via a purge gas conduit 72. As examples, purge gas stream 74 may include and/or be a dry, or at least substantially dry, purge gas stream; a low humidity purge gas stream; an inert purge gas stream; and/or an oxygen-free, or at least substantially oxygen-free, purge gas stream. Environmental control assembly 70 may include a purge gas source 71 configured to generate purge gas stream 74.

Probe system 20 also may be configured to provide, modify, control, and/or regulate an atmospheric environment within a portion of enclosure volume 32 that is external to shielded volume 202. For example, purge gas stream 74 may be a first purge gas stream 74, and environmental control assembly 70 additionally may be configured to provide a second purge gas stream 78 to a portion of enclosure volume 32 that is external to shielded volume 202. Similarly, in an embodiment that includes second purge gas stream 78, purge gas conduit 72 may be a first purge gas conduit 72, and environmental control assembly 70 additionally may include a second purge gas conduit 76 configured to provide second purge gas stream 78 to a portion of enclosure volume 32 that is external to shielded volume 202.

As discussed, temperature-controlled chuck 110 is configured to regulate a temperature of support surface 152, and thereby to regulate a temperature of substrate 90 and/or DUT 92. Specifically, temperature-controlled chuck 110 may be configured to regulate a temperature of substrate 90 and/or DUT 92 over a test temperature range. As examples, the test temperature range may extend over at least 100 degrees Celsius, at least 150 degrees Celsius, at least 200 degrees Celsius, at least 250 degrees Celsius, at least 300 degrees Celsius, at least 350 degrees Celsius, at least 400 degrees Celsius, at least 450 degrees Celsius, and/or at least 500 degrees Celsius.

The test temperature range may extend between a minimum test temperature and a maximum test temperature. Examples of the minimum test temperature include minimum test temperatures of at least −200° C., at least −150° C., at least −100° C., at least −50° C., at least 0° C., and/or at least 50° C. Examples of the maximum test temperature include maximum test temperatures of at most 100° C., at most 150° C., at most 200° C., at most 250° C., at most 300° C., at most 350° C., or at most 400° C.

With continued reference to FIGS. 2-3, temperature-controlled chuck 110 may include an electrically conductive upper chuck layer 120 positioned between upper electrically insulating layer 140 and a remainder of temperature-controlled chuck 110. Electrically conductive upper chuck layer 120 also may be referred to herein as an upper chuck layer 120. Upper chuck layer 120 may be in electrical communication, and/or in direct electrical communication, with at least a portion of shielding structure 200. Additionally or alternatively, in an embodiment that includes guard conductor 62, guard conductor 62 may be in electrical communication with upper chuck layer 120 and/or may be configured to maintain upper chuck layer 120 at the shield potential and/or at the guard potential.

Temperature-controlled chuck 110 additionally may include a lower electrically insulating layer 130 that extends between upper chuck layer 120 and at least a portion of shielding structure 200. Lower electrically insulating layer 130 may be thermally conductive, and may be configured to facilitate thermal exchange between temperature-controlled chuck 110 and support surface 152 and/or between a remainder of temperature-controlled chuck 110 and support surface 152. However, lower electrically insulating layer 130 also may electrically isolate upper chuck layer 120 and/or temperature-controlled chuck 110 from electrically conductive shielding structure 200.

As discussed, upper stack layer 150 may be configured to support substrate 90 via support surface 152. As illustrated in FIGS. 2-3, upper stack layer 150 additionally may include a vacuum distribution manifold 154 configured to apply a retention vacuum to support surface 152 to retain substrate 90 on support surface 152. Vacuum distribution manifold 154 may be coupled to a vacuum source 156 via a vacuum conduit 158.

Enclosure 30 may include and/or be any suitable structure that may define enclosure volume 32 and/or that may house and/or contain at least a portion of contacting assembly 50, substrate 90, and/or DUT 92. In addition, enclosure 30 also may be configured to shield and/or protect at least a portion of contacting assembly 50, substrate 90, and/or DUT 92 from the ambient environment that surrounds probe system 20. Specifically, enclosure 30 may be configured to shield support surface 152, substrate 90, and/or DUT 92 from electromagnetic radiation generated external to enclosure volume 32. For example, enclosure 30 may be formed from an electromagnetically shielding material. Additionally or alternatively, enclosure 30 may be an electrically conductive enclosure, may be a metallic enclosure, and/or may be an electrically shielded enclosure. Additionally or alternatively, enclosure 30 may be configured to thermally insulate support surface 152, substrate 90, and/or DUT 92 from the ambient environment that surrounds enclosure 30.

As examples, enclosure 30 may include and/or be a sealed, fluidly sealed, and/or hermetically sealed enclosure. As additional examples, enclosure 30 may be configured to restrict transmission of ambient light and/or other electromagnetic radiation into enclosure volume 32. As yet another example, enclosure 30 may be configured to provide shielding for DUT 92 and/or probe 56 from electromagnetic radiation. As another example, enclosure 30 may include one or more walls, which may at least partially bound enclosure volume 32.

As discussed, translation stage 40 is configured to operatively translate and/or rotate substrate-supporting stack 100. More specifically, translation stage 40 may be configured to operatively and/or simultaneously translate substrate-supporting stack 100, isolation structure 300, thermal shielding structure 400, and/or at least a portion of electrically conductive shielding structure 200 relative to enclosure 30 along a first axis and along a second axis that is perpendicular, or at least substantially perpendicular, to the first axis. The first axis and the second axis may both be parallel, or at least substantially parallel, to support surface 152. For example, the first axis may be oriented in the X-direction as illustrated in FIGS. 1-3, and/or the second axis may be oriented in the Y-direction as illustrated in FIGS. 1-3.

Translation stage 40 additionally may be configured to operatively and/or simultaneously translate substrate-supporting stack 100, isolation structure 300, thermal shielding structure 400, and/or at least a portion of electrically conductive shielding structure 200 relative to enclosure 30 along a third axis that is perpendicular, or at least substantially perpendicular, to support surface 152. For example, the third axis may be oriented in the Z-direction as illustrated in FIGS. 1-3.

Additionally or alternatively, translation stage 40 may be configured to operatively and/or simultaneously rotate substrate-supporting stack 100, isolation structure 300, thermal shielding structure 400, and/or at least a portion of electrically conductive shielding structure 200 about a rotation axis. The rotation axis may be perpendicular, or at least substantially perpendicular, to support surface 152, and/or may be the third axis.

As discussed, probe system 20 may include contacting assembly 50 configured to contact DUT 92 with one or more probe tips 58 of a corresponding one or more probes 56. More specifically, and with reference to FIGS. 2-3, contacting assembly 50 may include a plurality of probe tips 58, and each of the plurality of probe tips 58 may be configured to provide a corresponding test signal 86 to DUT 92 and/or to receive a corresponding resultant signal 88 from DUT 92.

Test signal 86 may include, or be, a direct current test signal and/or an alternating current test signal. Contacting assembly 50 additionally or alternatively may include a probe head assembly 52 that includes the plurality of probe tips 58 and/or a corresponding plurality of probes 56. Additionally or alternatively, probe system 20 may include a signal generation and analysis assembly 84 that is configured to provide corresponding test signal 86 to contacting assembly 50 and/or to receive corresponding resultant signal 88 from the contacting assembly.

Manipulator 53 may include and/or be any suitable structure that may be operatively attached to probe 56, such as via probe arm 55, and/or that may be configured to operatively translate probe 56 throughout the probe range-of-motion. As discussed, manipulator 53 may be external to enclosure volume 32 and/or may be operatively attached to platen 80. As also discussed, the probe arm range-of-motion may extend in three orthogonal, or at least substantially orthogonal, axes, such as the X, Y, and Z-axes of FIGS. 1-3.

Manipulator 53 may include any suitable structure. As examples, manipulator 53 may include one or more translation stages, lead screws, ball screws, rack and pinion assemblies, motors, stepper motors, electrical actuators, mechanical actuators, micrometers, and/or manual actuators. Manipulator 53 may be a manually actuated manipulator and/or an automated, or electrically actuated, manipulator.

Substrate 90 may include and/or be any suitable structure that may support, include, and/or have formed thereon DUT 92. Examples of substrate 90 include a wafer, a semiconductor wafer, a silicon wafer, and/or a gallium arsenide wafer.

Similarly, DUT 92 may include and/or be any suitable structure that may be probed and/or tested by probe system 20. As examples, DUT 92 may include a semiconductor device, an electronic device, an optical device, a logic device, a power device, a switching device, and/or a transistor.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B," when used in conjunction with open-ended language such as "comprising" may refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entity in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" may mean A alone, B alone, C alone, A and B together, A and C together, B and C together, A, B and C together, and optionally any of the above in combination with at least one other entity.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally. As used herein the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa.

As used herein, the phrase, "for example," the phrase, "as an example," and/or simply the term "example," when used with reference to one or more components, features, details, structures, and/or embodiments according to the present disclosure, are intended to convey that the described component, feature, detail, structure, and/or embodiment is an illustrative, non-exclusive example of components, features, details, structures, and/or embodiments according to the present disclosure. Thus, the described component, feature, detail, structure, and/or embodiment is not intended to be limiting, required, or exclusive/exhaustive; and other components, features, details, structures, and/or embodiments, including structurally and/or functionally similar and/or equivalent components, features, details, structures, and/or embodiments, are also within the scope of the present disclosure.

Illustrative, non-exclusive examples of probe systems according to the present disclosure are presented in the following enumerated paragraphs.

A1. A shielded probe system for testing a device under test (DUT), the probe system comprising:

an enclosure defining an enclosure volume;

a translation stage including a stage surface that extends within the enclosure volume;

a substrate-supporting stack extending from the stage surface and within the enclosure volume, wherein the substrate-supporting stack includes an electrically conductive support surface, which is configured to support a substrate that includes the DUT, and a temperature-controlled chuck, which is configured to regulate a temperature of the electrically conductive support surface;

an electrically conductive shielding structure extending within the enclosure volume and defining a shielded volume that contains the electrically conductive support surface, wherein the shielded volume is a subset of the enclosure volume, and further wherein the electrically conductive shielding structure extends between the electrically conductive support surface and the enclosure, the translation stage, and the temperature-controlled chuck;

an isolation structure that electrically isolates the electrically conductive shielding structure from the enclosure and from the translation stage; and a thermal shielding structure extending within the enclosure volume and at least partially between the enclosure and the substrate-supporting stack.

A2. The shielded probe system of paragraph A1, wherein the electrically conductive shielding structure is configured to shield the electrically conductive support surface from electromagnetic radiation that is generated external to the shielded volume.

A3. The shielded probe system of any of paragraphs A1-A2, wherein the electrically conductive shielding structure includes an electrically conductive peripheral shield that is spaced-apart from the substrate-supporting stack and extends around an external periphery of the substrate-supporting stack.

A4. The shielded probe system of paragraph A3, wherein the electrically conductive peripheral shield and the substrate-supporting stack together define an annular region that defines at least a portion of the shielded volume.

A5. The shielded probe system of any of paragraphs A3-A4, wherein the electrically conductive shielding structure further includes a flexible, electrically conductive lower shield that extends between the substrate-supporting stack and the electrically conductive peripheral shield.

A6. The shielded probe system of paragraph A5, wherein the electrically conductive lower shield fluidly isolates the shielded volume from the temperature-controlled chuck.

A7. The shielded probe system of any of paragraphs A5-A6, wherein the electrically conductive lower shield further extends between the temperature-controlled chuck and the electrically conductive support surface.

A8. The shielded probe system of any of paragraphs A5-A7, wherein the electrically conductive lower shield is configured to limit heat transfer from the temperature-controlled chuck to the electrically conductive peripheral shield.

A9. The shielded probe system of any of paragraphs A5-A8, wherein the electrically conductive lower shield includes at least one of a metal foil, a metallic foil, a nickel foil, a metal-coated membrane, and an electrically conductive membrane.

A10. The shielded probe system of any of paragraphs A5-A9, wherein the electrically conductive lower shield is configured to permit relative motion between the electrically conductive peripheral shield and the substrate-supporting stack.

A11. The shielded probe system of any of paragraphs A5-A10, wherein the electrically conductive lower shield includes at least one expansion region configured to permit relative motion between the electrically conductive peripheral shield and the substrate-supporting stack.

A12. The shielded probe system of paragraph A11, wherein the expansion region is configured to at least one of expand and contract to permit the relative motion between the electrically conductive peripheral shield and the substrate-supporting stack.

A13. The shielded probe system of any of paragraphs A11-A12, wherein the expansion region includes at least one pleat.

A14. The shielded probe system of any of paragraphs A1-A13, wherein the electrically conductive shielding structure further includes an electrically conductive upper shield that extends above the electrically conductive support surface.

A15. The shielded probe system of paragraph A14, wherein the electrically conductive upper shield includes an aperture sized to permit at least one probe, optionally a plurality of probes, and further optionally a plurality of spaced-apart probes, to extend therethrough.

A16. The shielded probe system of any of paragraphs A14-A15, when dependent upon paragraph A3, wherein the electrically conductive shielding structure further includes an electrically conductive gasket that extends between the electrically conductive peripheral shield and the electrically conductive upper shield.

A17. The shielded probe system of paragraph A16, wherein the electrically conductive gasket is configured to form an at least partial fluid seal between the electrically conductive peripheral shield and the electrically conductive upper shield.

A18. The shielded probe system of any of paragraphs A16-A17, wherein the electrically conductive gasket is configured to restrict electromagnetic radiation from entering the shielded volume.

A19. The shielded probe system of any of paragraphs A16-A18, wherein the electrically conductive gasket includes a resilient gasket, and optionally a foam gasket.

A20. The shielded probe system of any of paragraphs A16-A19, wherein the electrically conductive gasket includes an inflatable gasket configured to be:
 (i) selectively inflated to selectively contact the electrically conductive upper shield; and
 (ii) selectively deflated to retract from the electrically conductive upper shield.

A21. The shielded probe system of paragraph A20, wherein the shielded probe system further includes a pressurizing fluid source configured to selectively inflate the inflatable gasket and to selectively deflate the inflatable gasket.

A22. The shielded probe system of any of paragraphs A16-A21, wherein the electrically conductive shielding structure is configured to selectively contact the electrically conductive gasket with the electrically conductive upper shield and to selectively retract the electrically conductive gasket from the electrically conductive upper shield.

A23. The shielded probe system of any of paragraphs A16-A22, wherein the electrically conductive shielding structure further includes a drive mechanism configured to selectively contact the electrically conductive gasket with the electrically conductive upper shield and to selectively retract the electrically conductive gasket from the electrically conductive upper shield.

A24. The shielded probe system of any of paragraphs A16-A23, wherein the translation stage is configured to selectively contact the electrically conductive gasket with the electrically conductive upper shield and to selectively retract the electrically conductive gasket from the electrically conductive upper shield.

A25. The shielded probe system of any of paragraphs A1-A24, wherein the electrically conductive shielding structure is at least one of metallic and metal-coated.

A26. The shielded probe system of any of paragraphs A1-A25, wherein the temperature-controlled chuck is external to the shielded volume.

A27. The shielded probe system of any of paragraphs A1-A26, wherein the translation stage is external to the shielded volume.

A28. The shielded probe system of any of paragraphs A1-A27, wherein the isolation structure is external to the shielded volume.

A29. The shielded probe system of any of paragraphs A1-A28, wherein the isolation structure is formed from an electrically insulating material.

A30. The shielded probe system of any of paragraphs A1-A29, wherein the isolation structure is formed from a thermally insulating material.

A31. The shielded probe system of any of paragraphs A1-A30, wherein the isolation structure forms a portion of the thermal shielding structure.

A32. The shielded probe system of any of paragraphs A1-A31, wherein the isolation structure extends between at least a portion of the electrically conductive shielding structure and the translation stage.

A33. The shielded probe system of any of paragraphs A1-A32, wherein the isolation structure spatially separates the electrically conductive shielding structure from the translation stage.

A34. The shielded probe system of any of paragraphs A1-A33, wherein the isolation structure is operatively attached to the stage surface of the translation stage.

A35. The shielded probe system of any of paragraphs A1-A34, wherein the isolation structure is operatively attached to the electrically conductive shielding structure.

A36. The shielded probe system of any of paragraphs A1-A35, wherein the thermal shielding structure is formed from a/the thermally insulating material.

A37. The shielded probe system of any of paragraphs A1-A36, wherein the thermal shielding structure surrounds at least a portion of the electrically conductive shielding structure.

A38. The shielded probe system of paragraph A37, wherein the at least a portion of the electrically conductive shielding structure includes an external periphery of a/the electrically conductive peripheral shield.

A39. The shielded probe system of paragraph A38, wherein the thermal shielding structure is spaced-apart from the external periphery of the electrically conductive peripheral shield.

A40. The shielded probe system of paragraph A38, wherein the thermal shielding structure is in direct physical contact with the external periphery of the electrically conductive peripheral shield.

A41. The shielded probe system of any of paragraphs A1-A40, wherein the thermal shielding structure extends between at least a portion of the electrically conductive shielding structure and at least a portion of the enclosure.

A42. The shielded probe system of any of paragraphs A1-A41, wherein the thermal shielding structure extends between the temperature-controlled chuck and the translation stage.

A43. The shielded probe system of any of paragraphs A1-A42, wherein the thermal shielding structure is operatively attached to the stage surface of the translation stage.

A44. The shielded probe system of any of paragraphs A1-A43, wherein the thermal shielding structure is operatively attached to the substrate-supporting stack.

A45. The shielded probe system of any of paragraphs A1-A44, wherein the enclosure is an electrically conductive enclosure.

A46. The shielded probe system of paragraph A45, wherein the shielded probe system further includes a shield conductor that is in electrical communication with the enclosure and configured to at least one of:
 (i) maintain the enclosure at a shield potential; and
 (ii) ground the enclosure.

A47. The shielded probe system of paragraph A46, wherein the shielded probe system further includes a shield potential generator configured to generate the shield potential.

A48. The shielded probe system of any of paragraphs A1-A47, wherein the shielded probe system further includes a guard conductor that is in electrical communication with the electrically conductive shielding structure and configured to at least one of:
 (i) maintain the electrically conductive shielding structure at a guard potential; and
 (i) ground the electrically conductive shielding structure.

A49. The shielded probe system of paragraph A48, wherein the shielded probe system further includes a guard potential generator configured to generate the guard potential.

A50. The shielded probe system of any of paragraphs A48-A49, when dependent upon paragraph A46, wherein the guard potential is different from a/the shield potential of the enclosure.

A51. The shielded probe system of any of paragraphs A48-A49, when dependent upon paragraph A46, wherein the guard potential is equal to the shield potential.

A52. The shielded probe system of any of paragraphs A48-A51, wherein the probe system further includes a switching structure configured to selectively apply the guard potential to the guard conductor and to selectively ground the guard conductor.

A53. The shielded probe system of any of paragraphs A1-A52, wherein the shielded probe system further includes an environmental control assembly configured to provide a purge gas stream to the shielded volume to regulate a chemical composition of a testing environment that extends within the shielded volume.

A54. The shielded probe system of paragraph A53, wherein the environmental control assembly includes a purge gas conduit configured to provide the purge gas stream to the shielded volume.

A55. The shielded probe system of any of paragraphs A53-A54, wherein the purge gas stream includes at least one of:
 (i) a dry, or at least substantially dry, purge gas stream;
 (ii) a low humidity purge gas stream;
 (iii) an inert purge gas stream; and
 (iv) an oxygen-free, or at least substantially oxygen-free, purge gas stream.

A56. The shielded probe system of any of paragraphs A53-A55, wherein the environmental control assembly further includes a purge gas source configured to generate the purge gas stream.

A57. The shielded probe system of any of paragraphs A53-A56, wherein the purge gas stream is a first purge gas stream, and further wherein the environmental control assembly is configured to provide a second purge gas stream to a portion of the enclosure volume that is external to the shielded volume.

A58. The shielded probe system of any of paragraphs A54-A57, wherein the purge gas conduit is a first purge gas conduit, and further wherein the environmental control assembly includes a second purge gas conduit configured to provide the second purge gas stream to the portion of the enclosure volume that is external to the shielded volume.

A59. The shielded probe system of any of paragraphs A1-A58, wherein the temperature-controlled chuck is configured to regulate a temperature of the substrate over a test temperature range.

A60. The shielded probe system of paragraph A59, wherein the test temperature range extends over at least 100 degrees Celsius, at least 150 degrees Celsius, at least 200 degrees Celsius, at least 250 degrees Celsius, at least 300 degrees Celsius, at least 350 degrees Celsius, at least 400 degrees Celsius, at least 450 degrees Celsius, or at least 500 degrees Celsius.

A61. The shielded probe system of any of paragraphs A1-A60, wherein the temperature-controlled chuck includes an electrically conductive upper chuck layer.

A62. The shielded probe system of paragraph A61, wherein the shielded probe system further includes a/the guard conductor that is in electrical communication with the electrically conductive upper chuck layer and configured to maintain the electrically conductive upper chuck layer at one of:
 (i) a/the shield potential; and
 (ii) a/the guard potential.

A63. The shielded probe system of any of paragraphs A61-A62, wherein the electrically conductive upper chuck layer is in electrical communication, and optionally in direct electrical communication, with at least a portion of the electrically conductive shielding structure.

A64. The shielded probe system of any of paragraphs A61-A63, wherein the substrate-supporting stack further includes a lower electrically insulating layer that extends between the electrically conductive upper chuck layer and at least a portion of the electrically conductive shielding structure.

A65. The shielded probe system of paragraph A64, wherein the lower electrically insulating layer is a thermally conductive lower electrically insulating layer configured to facilitate thermal exchange between the temperature-controlled chuck and the electrically conductive support surface.

A66. The shielded probe system of any of paragraphs A1-A65, wherein the substrate-supporting stack further includes an electrically conductive upper stack layer that defines the electrically conductive support surface.

A67. The shielded probe system of paragraph A66, wherein the electrically conductive upper stack layer is at least one of:
 thermally conductive; and
 (ii) metallic.

A68. The shielded probe system of any of paragraphs A66-A67, wherein the electrically conductive upper stack layer includes a vacuum distribution manifold configured to apply a retention vacuum to the electrically conductive support surface to retain the substrate on the electrically conductive support surface.

A69. The shielded probe system of any of paragraphs A66-A68, wherein the substrate-supporting stack further includes an upper electrically insulating layer that extends between the temperature-controlled chuck and the electrically conductive upper stack layer.

A70. The shielded probe system of paragraph A69, wherein the upper electrically insulating layer further extends between the electrically conductive upper stack layer and at least a portion of the electrically conductive shielding structure.

A71. The shielded probe system of any of paragraphs A69-A70, wherein the upper electrically insulating layer is a thermally conductive upper electrically insulating layer configured to facilitate thermal exchange between the temperature-controlled chuck and the electrically conductive upper stack layer.

A72. The shielded probe system of any of paragraphs A1-A71, wherein the enclosure is at least one of an electrically conductive enclosure and a metallic enclosure.

A73. The shielded probe system of any of paragraphs A1-A72, wherein the enclosure is configured to shield the electrically conductive support surface from electromagnetic radiation that is generated external to the enclosure volume.

A74. The shielded probe system of any of paragraphs A1-A72, wherein the enclosure is formed from an electromagnetically shielding material.

A75. The shielded probe system of any of paragraphs A1-A74, wherein the enclosure is configured to thermally insulate the electrically conductive support surface from an ambient environment that surrounds the enclosure.

A76. The shielded probe system of any of paragraphs A1-A75, wherein a ratio of a volume of the shielded volume to a volume of the enclosure volume is at least one of:
 (i) at least 0.001, at least 0.005, at least 0.01, at least 0.05, at least 0.1, at least 0.15, at least 0.2, or at least 0.25; and
 (ii) at most 0.5, at most 0.4, at most 0.3, at most 0.25, at most 0.2, at most 0.15, or at most 0.1.

A77. The shielded probe system of any of paragraphs A1-A76, wherein the translation stage is configured to operatively translate the substrate-supporting stack, the isolation structure, the thermal shielding structure, and at least a portion of the electrically conductive shielding structure relative to the enclosure along a first axis and along a second axis that is perpendicular to the first axis.

A78. The shielded probe system of paragraph A77, wherein the first axis and the second axis both are parallel, or at least substantially parallel, to the electrically conductive support surface.

A79. The shielded probe system of any of paragraphs A77-A78, wherein the translation stage further is configured to operatively translate the substrate-supporting stack, the isolation structure, the thermal shielding structure, and at least a portion of the electrically conductive shielding structure relative to the enclosure along a third axis that is perpendicular, or at least substantially perpendicular, to the electrically conductive support surface.

A80. The shielded probe system of any of paragraphs A1-A79, wherein the translation stage is configured to operatively rotate the substrate-supporting stack, the isolation structure, the thermal shielding structure, and at least a portion of the electrically conductive shielding structure about a rotational axis.

A81. The shielded probe system of paragraph A80, wherein the rotational axis is perpendicular to the electrically conductive support surface.

A82. The shielded probe system of any of paragraphs A80-A81, wherein the rotational axis is a/the third axis.

A83. The shielded probe system of any of paragraphs A1-A82, wherein the shielded probe system further includes a contacting assembly including a plurality of probe tips, wherein each of the plurality of probe tips is configured to at least one of:
 (i) provide a corresponding test signal to the DUT; and
 (ii) receive a corresponding resultant signal from the DUT.

A84. The shielded probe system of paragraph A83, wherein the test signal includes a direct current test signal.

A85. The shielded probe system of any of paragraphs A83-A84, wherein the test signal includes an alternating current test signal.

A86. The shielded probe system of any of paragraphs A83-A85, wherein the shielded probe system further includes a platen that extends above the electrically conductive support surface and is configured to support the contacting assembly.

A87. The shielded probe system of any of paragraphs A83-A86, wherein the contacting assembly includes a probe head assembly.

A88. The shielded probe system of any of paragraphs A83-A87, wherein the contacting assembly includes at least one probe arm, and optionally a plurality of probe arms.

A89. The shielded probe system of any of paragraphs A83-A88, wherein the shielded probe system further includes a signal generation and analysis assembly configured to provide the corresponding test signal to the DUT and receive the corresponding resultant signal from the DUT.

INDUSTRIAL APPLICABILITY

The probe systems disclosed herein are applicable to the semiconductor manufacturing and test industries.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. A shielded probe system for testing a device under test (DUT), the probe system comprising:
 an enclosure defining an enclosure volume;
 a translation stage including a stage surface that extends within the enclosure volume;
 a substrate-supporting stack extending from the stage surface and within the enclosure volume, wherein the substrate-supporting stack includes an electrically conductive support surface, which is configured to support a substrate that includes the DUT, and a temperature-controlled chuck, which is configured to regulate a temperature of the electrically conductive support surface;

an electrically conductive shielding structure extending within the enclosure volume and defining a shielded volume that contains the electrically conductive support surface, wherein the shielded volume is a subset of the enclosure volume, and further wherein the electrically conductive shielding structure extends between the electrically conductive support surface and the enclosure, the translation stage, and the temperature-controlled chuck;

an isolation structure that electrically isolates the electrically conductive shielding structure from the enclosure and from the translation stage; and a thermal shielding structure extending within the enclosure volume and at least partially between the enclosure and the substrate-supporting stack.

2. The shielded probe system of claim 1, wherein the electrically conductive shielding structure is configured to shield the electrically conductive support surface from electromagnetic radiation that is generated external to the shielded volume, and further wherein the electrically conductive shielding structure includes an electrically conductive peripheral shield that is spaced-apart from the substrate-supporting stack and extends around an external periphery of the substrate-supporting stack.

3. The shielded probe system of claim 2, wherein the electrically conductive shielding structure further includes a flexible, electrically conductive lower shield that extends between the substrate-supporting stack and the electrically conductive peripheral shield, and further wherein the electrically conductive lower shield fluidly isolates the shielded volume from the temperature-controlled chuck.

4. The shielded probe system of claim 3, wherein the electrically conductive lower shield is configured to permit relative motion between the electrically conductive peripheral shield and the substrate-supporting stack.

5. The shielded probe system of claim 1, wherein the electrically conductive shielding structure further includes an electrically conductive upper shield that extends above the electrically conductive support surface.

6. The shielded probe system of claim 5, wherein the electrically conductive shielding structure includes an electrically conductive peripheral shield that is spaced-apart from the substrate-supporting stack and extends around an external periphery of the substrate-supporting stack, wherein the electrically conductive shielding structure further includes an electrically conductive gasket that extends between the electrically conductive peripheral shield and the electrically conductive upper shield, and further wherein the electrically conductive gasket is configured to restrict electromagnetic radiation from entering the shielded volume.

7. The shielded probe system of claim 6, wherein the electrically conductive shielding structure is configured to selectively contact the electrically conductive gasket with the electrically conductive upper shield and to selectively retract the electrically conductive gasket from the electrically conductive upper shield.

8. The shielded probe system of claim 1, wherein the temperature-controlled chuck, the translation stage, and the isolation structure each are external to the shielded volume.

9. The shielded probe system of claim 1, wherein the isolation structure spatially separates the electrically conductive shielding structure from the translation stage.

10. The shielded probe system of claim 1, wherein the thermal shielding structure surrounds at least a portion of the electrically conductive shielding structure.

11. The shielded probe system of claim 10, wherein the at least a portion of the electrically conductive shielding structure includes an external periphery of an electrically conductive peripheral shield, and further wherein the thermal shielding structure is spaced-apart from the external periphery of the electrically conductive peripheral shield.

12. The shielded probe system of claim 1, wherein the enclosure is an electrically conductive enclosure, and wherein the shielded probe system further includes a shield conductor that is in electrical communication with the enclosure and configured to at least one of:
  (i) maintain the enclosure at a shield potential; and
  (ii) ground the enclosure.

13. The shielded probe system of claim 1, wherein the shielded probe system further includes a guard conductor that is in electrical communication with the electrically conductive shielding structure and configured to at least one of:
  (i) maintain the electrically conductive shielding structure at a guard potential; and
  (ii) ground the electrically conductive shielding structure.

14. The shielded probe system of claim 13, wherein the probe system further includes a switching structure configured to selectively apply the guard potential to the guard conductor and to selectively ground the guard conductor.

15. The shielded probe system of claim 1, wherein the shielded probe system further includes an environmental control assembly configured to provide a purge gas stream to the shielded volume to regulate a chemical composition of a testing environment that extends within the shielded volume.

16. The shielded probe system of claim 1, wherein the temperature-controlled chuck includes an electrically conductive upper chuck layer, and wherein the shielded probe system further includes a guard conductor that is in electrical communication with the electrically conductive upper chuck layer and configured to maintain the electrically conductive upper chuck layer at one of:
  (i) a shield potential; and
  (ii) a guard potential.

17. The shielded probe system of claim 16, wherein the substrate-supporting stack further includes a lower electrically insulating layer that extends between the electrically conductive upper chuck layer and at least a portion of the electrically conductive shielding structure, and further wherein the lower electrically insulating layer is a thermally conductive lower electrically insulating layer configured to facilitate thermal exchange between the temperature-controlled chuck and the electrically conductive support surface.

18. The shielded probe system of claim 1, wherein the substrate-supporting stack further includes an electrically conductive upper stack layer that defines the electrically conductive support surface, wherein the substrate-supporting stack further includes an upper electrically insulating layer that extends between the temperature-controlled chuck and the electrically conductive upper stack layer, wherein the upper electrically insulating layer further extends between the electrically conductive upper stack layer and at least a portion of the electrically conductive shielding structure, and further wherein the upper electrically insulating layer is a thermally conductive upper electrically insulating layer configured to facilitate thermal exchange between the temperature-controlled chuck and the electrically conductive upper stack layer.

19. The shielded probe system of claim 1, wherein a ratio of a volume of the shielded volume to a volume of the enclosure volume is at least 0.001 and at most 0.25.

20. The shielded probe system of claim 1, wherein the shielded probe system further includes a contacting assembly including a plurality of probe tips, wherein each of the plurality of probe tips is configured to at least one of:
  (i) provide a corresponding test signal to the DUT; and
  (ii) receive a corresponding resultant signal from the DUT.

* * * * *